(12) United States Patent
Takagi et al.

(10) Patent No.: US 8,114,649 B2
(45) Date of Patent: Feb. 14, 2012

(54) L-CYSTEINE PRODUCING MICROORGANISM AND A METHOD FOR PRODUCING L-CYSTEINE

(75) Inventors: Hiroshi Takagi, Fukui (JP); Shigeru Nakamori, Fukui (JP); Masaru Wada, Fukui (JP); Hirotada Mori, Ikoma (JP)

(73) Assignee: Ajinomoto Co., Inc., Tokyo (JP)

( * ) Notice: Subject to any disclaimer, the term of this patent is extended or adjusted under 35 U.S.C. 154(b) by 113 days.

(21) Appl. No.: 12/635,404

(22) Filed: Dec. 10, 2009

(65) Prior Publication Data

US 2010/0093045 A1    Apr. 15, 2010

Related U.S. Application Data

(62) Division of application No. 11/070,084, filed on Mar. 30, 2005, now abandoned.

(30) Foreign Application Priority Data

Mar. 4, 2004    (JP) .................................. 2004-060483

(51) Int. Cl.
*C12N 9/00* (2006.01)
*C12N 9/10* (2006.01)
*C12P 13/12* (2006.01)
*C12N 1/20* (2006.01)

(52) U.S. Cl. ..... 435/183; 435/113; 435/193; 435/252.3; 435/252.8

(58) Field of Classification Search .................. 435/183, 435/193, 113, 252.3, 252.8
See application file for complete search history.

(56) References Cited

U.S. PATENT DOCUMENTS

| | | | |
|---|---|---|---|
| 7,052,896 B2 | 5/2006 | Glenn et al. | |
| 7,312,058 B2 | 12/2007 | Kashiwagi et al. | |
| 7,745,195 B2 * | 6/2010 | Chateau et al. | 435/243 |
| 2005/0112731 A1 | 5/2005 | Kashiwagi et al. | |

FOREIGN PATENT DOCUMENTS

| | | |
|---|---|---|
| EP | 1 298 200 | 4/2003 |
| JP | 11155571 | 6/1999 |
| WO | WO 97/15673 | 5/1997 |
| WO | WO 2004/076659 | 9/2004 |

OTHER PUBLICATIONS

Awano, N., et al., Effect of cysteine desulfhydrase gene disruption on L-cysteine overproduction in *Escherichia coli*,: Appl. Microbiol. Biotechnol. 2003;62:239-243.

Clausen, T., et al., "X-ray structure of MalY from *Escherichia coli*: a pyridoxal 5'-phosphate-dependent enzyme acting as a modulator in mal gene expression," The EMBO Journal 2000;19(5):831-842.

Flint, D. H., et al., "Studies on the Synthesis of the Fe-S Cluster of Dihydroxy-acid Dehydratase in *Escherichia coli* Crude Extract," J. Biol. Chem 1996;271(27):16053-16067.

Garvis, S. G., et al., "Identification of a functional homolog of the *Escherichia coli* and *Salmonella typhimurium* cysM gene encoding 0-acetylserine sulfhydrylase B in *Campylobacter jejuni*," Gene 1997;185:63-67.

Reidl, J., et al., "The *malX malY* Operon of *Escherichia coli* Encodes a Novel Enzyme II of the Phosphotransferase System Recognizing Glucose and Maltose and an Enzyme Abolishing the Endogenous Induction of the Maltose System," J. Bacterial. 1991;173(15):4862-4876.

Sekowska, A., et al., "Sulfur Metabolism in *Escherichia coli* and Related Bacteria: Facts and Fiction," J. Mol. Microbiol. Biotechnol. 2000;2(2):145-177.

Sirko, A., et al., "Sulfate and Thiosulfate Transport in *Escherichia coli* K-12: Nucleotide Sequence and Expression of the *cysTWAM* Gene Cluster," J. Bacteriol. 1990;172(6):3351-3357.

Takagi, H., "Production of L-Cysteine," Patent Abstracts of Japan, Publ. No. 11155571 (Jun. 15, 1999).

Zdych, E., et al., "MalY of *Escherichia coli* Is an Enzyme with the Activity of a βC-S Lyase (Cystathionase)," J. Bacteriol. 1995;177(17):5035-5039.

Search Report for European Patent Appl. No. EP 05 00 4829 (Oct. 13, 2005).

Search Report for EP Appl. No. 05004829.7 (Jul. 12, 2005).

Sirko, A. F., et al., "Identification of the *Escherichia coli cysM* Gene Encoding O-Acetylserine Sulphydrylase B by Cloning with Mini-Mu-*lac* Containing a Plasmid Replicon," J. Gen. Microbiol. 1987;133:2719-2725.

European Search Report for EP Patent App. No. 07003442.6 (Sep. 28, 2007).

Notice of Reason for Rejection for Japanese Patent App. No. 2004-060483 (Nov. 17, 2009), with English translation thereof.

\* cited by examiner

*Primary Examiner* — Maria Leavitt
(74) *Attorney, Agent, or Firm* — Shelly Guest Cermak; Cermak Nakajima LLP

(57) ABSTRACT

L-cysteine is produced by culturing an *Escherichia* bacterium having L-cysteine producing ability and containing a gene encoding an O-acetylserine sulphydrylase B or MalY regulatory protein that is modified so that cysteine desulfhydrase activity is reduced or eliminated. The bacterium is cultured in a medium to produce and cause accumulation of L-cysteine in the medium, and collecting L-cysteine from the medium.

6 Claims, 3 Drawing Sheets

Fig. 2

DNA primer used for disruption of CD gene

| Primer name | used | Primer sequence |
|---|---|---|
| gd tnaA-1 | Disruption of E. coli tnaA gene | 5'-CGC GGA TCC AAG CCG CAT TCT GAC TG-3' (SEQ ID NO: 1) |
| gd tnaA-2 | Disruption of E. coli tnaA gene | 5'-CCC AAG CTT CTG ACT CGG GCT AAC GCA-3' (SEQ ID NO: 2) |
| gd tnaA-3 | Disruption of E. coli tnaA gene | 5'-CCC AAG CTT GCC GGT TTC ACT GGC AA-3' (SEQ ID NO: 3) |
| gd tnaA-4 | Disruption of E. coli tnaA gene | 5'-CTA TGG ATC CTT ATA GCC ACT CTG TAG-3' (SEQ ID NO: 4) |
| gd tnaA-FW | Confirmation of tnaA gene disruption | 5'-CTA TGG ATC CTT ATA GCC ACT CTG TAG-3' (SEQ ID NO: 5) |
| gd tnaA-RV | Confirmation of tnaA gene disruption | 5'-CAC CGG GGA ATT TAC TTC AGA C-3' (SEQ ID NO: 6) |
| gd metC-1 | Disruption of E. coli metC gene | 5'-CGC GGA TCC AAC AGA CCT TCT GCG ATA CC-3' (SEQ ID NO: 7) |
| gd metC-2 | Disruption of E. coli metC gene | 5'-CGG GGT ACC ACT AGC ATG AAT ATT CGC GG-3' (SEQ ID NO: 8) |
| gd metC-3 | Disruption of E. coli metC gene | 5'-CGG GGT ACC TAC CGC CTA TAT ATA ACC AGC C-3' (SEQ ID NO: 9) |
| gd metC-4 | Disruption of E. coli metC gene | 5'-AAT ATG AGG ATC CGC CAG C-3' (SEQ ID NO: 10) |
| gd metC-FW | Confirmation of metC gene disruption | 5'-GTT ATA GAT AAC GAC CGC AGG-3' (SEQ ID NO: 11) |
| gd metC-RV | Confirmation of metC gene disruption | 5'-CGC CCC TGA ATA TAA CTT AG-3' (SEQ ID NO: 12) |
| gd cysM-1 | Disruption of E. coli cysM gene | 5'-GCG GCG GGA TCC TAG GTT GAG TGA ATG TTA AAC GCC C-3' (SEQ ID NO: 13) |
| gd cysM-2 | Disruption of E. coli cysM gene | 5'-GGG GGG AAG CTT GGT GTT ACC ACT GGT GGC TTC GAT T-3' (SEQ ID NO: 14) |
| gd cysM-3 | Disruption of E. coli cysM gene | 5'-GGG GGC AAG CTT AAT ATT CTG IGG CGT CAG CTC CGG C-3' (SEQ ID NO: 15) |
| gd cysM-4 | Disruption of E. coli cysM gene | 5'-GCG GCG GGA TCC ATA CTG CAT TTG TCG GCA GCA ACA-3' (SEQ ID NO: 16) |
| gd cysM-FW | Confirmation of cysM gene disruption | 5'-AAC CCG CGA TGA GGA ACT TGC TCT C-3' (SEQ ID NO: 17) |
| gd cysM-RV | Confirmation of cysM gene disruption | 5'-TTC AAT GAC CTT ACG GCG TTT CCT C-3' (SEQ ID NO: 18) |
| gd cysK-1 | Disruption of E. coli cysK gene | 5'-CGC CGC GGA TCC CAA TCT ACC GGT TAT TTT GAT AAC C-3' (SEQ ID NO: 19) |
| gd cysK-2 | Disruption of E. coli cysK gene | 5'-CGG CGG GGT ACC TTT TCG GCA TCC CAA ATC ATG TTG G-3' (SEQ ID NO: 20) |
| gd cysK-3 | Disruption of E. coli cysK gene | 5'-GCC GCC GGT ACC ATT AAA CCT GGC CCG CAT AAA ATT C-3' (SEQ ID NO: 21) |
| gd cysK-4 | Disruption of E. coli cysK gene | 5'-CGC CGC GGA TCC CAA GCT GGC ATT ACT GTT GCA ATT C-3' (SEQ ID NO: 22) |
| gd cysK-FW | Confirmation of cysK gene disruption | 5'-CTA TCG CGA TAA ACA CGC GAT GTG-3' (SEQ ID NO: 23) |
| gd cysK-RV | Confirmation of cysK gene disruption | 5'-GGC GAA AGT TTG AAG CAG GCC AC-3' (SEQ ID NO: 24) |
| gd malY-1 | Disruption of E. coli malY gene | 5'-ATC CAG TCG ATC ATC GAT ACC GGG ATC C-3' (SEQ ID NO: 25) |
| gd malY-2 | Disruption of E. coli malY gene | 5'-GGC GCT ACG AAC AAC AGG AAC AGG AAT TC-3' (SEQ ID NO: 26) |
| gd malY-3 | Disruption of E. coli malY gene | 5'-GGC CGA ATT CCG TCA TGG TGT GCG GGT TAT TTC CG-3' (SEQ ID NO: 27) |
| gd malY-4 | Disruption of E. coli malY gene | 5'-GCG GGG ATC CTT AAC GAA CAG CAG CGC GGA TGG CGT TA-3' (SEQ ID NO: 28) |
| gd malY-FW | Confirmation of malY gene disruption | 5'-TTC TGA AAG CCA ATA ACA TCC AGA G-3' (SEQ ID NO: 29) |
| gd malY-RV | Confirmation of malY gene disruption | 5'-GGT AAA AAT CCA CGA TTG CGC AAC G-3' (SEQ ID NO: 30) |

SEQUENCE LISTING

<160> NUMBER OF SEQ ID NOS: 36

<210> SEQ ID NO 1
<211> LENGTH: 26
<212> TYPE: DNA
<213> ORGANISM: Artificial
<220> FEATURE:
<223> OTHER INFORMATION: primer

<400> SEQUENCE: 1
cgcggatcca agccgcattc tgactg                                    26

<210> SEQ ID NO 2
<211> LENGTH: 27
<212> TYPE: DNA
<213> ORGANISM: Artificial
<220> FEATURE:
<223> OTHER INFORMATION: primer

<400> SEQUENCE: 2
cccaagcttc tgactcgggc taacgca                                   27

<210> SEQ ID NO 3
<211> LENGTH: 26
<212> TYPE: DNA
<213> ORGANISM: Artificial
<220> FEATURE:
<223> OTHER INFORMATION: primer

<400> SEQUENCE: 3
cccaagcttg ccggtttcac tggcaa                                    26

<210> SEQ ID NO 4
<211> LENGTH: 27
<212> TYPE: DNA
<213> ORGANISM: Artificial
<220> FEATURE:
<223> OTHER INFORMATION: primer

<400> SEQUENCE: 4
ctatggatcc ttatagccac tctgtag                                   27

<210> SEQ ID NO 5
<211> LENGTH: 27
<212> TYPE: DNA
<213> ORGANISM: Artificial
<220> FEATURE:
<223> OTHER INFORMATION: primer

<400> SEQUENCE: 5
ctatggatcc ttatagccac tctgtag                                   27

<210> SEQ ID NO 6
<211> LENGTH: 22
<212> TYPE: DNA
<213> ORGANISM: Artificial
<220> FEATURE:
<223> OTHER INFORMATION: primer

<400> SEQUENCE: 6
caccggggaa tttacttcag ac                                        22

<210> SEQ ID NO 7
<211> LENGTH: 29
<212> TYPE: DNA

<213> ORGANISM: Artificial
<220> FEATURE:
<223> OTHER INFORMATION: primer

<400> SEQUENCE: 7
cgcggatcca acagagcttc tgcgatacc                     29

<210> SEQ ID NO 8
<211> LENGTH: 29
<212> TYPE: DNA
<213> ORGANISM: Artificial
<220> FEATURE:
<223> OTHER INFORMATION: primer

<400> SEQUENCE: 8
cggggtacca ctagcatgaa tattcgcgg                     29

<210> SEQ ID NO 9
<211> LENGTH: 31
<212> TYPE: DNA
<213> ORGANISM: Artificial
<220> FEATURE:
<223> OTHER INFORMATION: primer

<400> SEQUENCE: 9
cggggtacct accgcctata tataaccagc c                  31

<210> SEQ ID NO 10
<211> LENGTH: 19
<212> TYPE: DNA
<213> ORGANISM: Artificial
<220> FEATURE:
<223> OTHER INFORMATION: primer

<400> SEQUENCE: 10
aatatgagga tccgccagc                                19

<210> SEQ ID NO 11
<211> LENGTH: 21
<212> TYPE: DNA
<213> ORGANISM: Artificial
<220> FEATURE:
<223> OTHER INFORMATION: primer

<400> SEQUENCE: 11
gttatagata acgaccgcag g                             21

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12
cgcccctgaa tataacttag                               20

<210> SEQ ID NO 13
<211> LENGTH: 37
<212> TYPE: DNA
<213> ORGANISM: Artificial
<220> FEATURE:
<223> OTHER INFORMATION: primer

<400> SEQUENCE: 13
gcggcgggat cctaggttga gtgaatgtta aacgccc             37

```
<210> SEQ ID NO 14
<211> LENGTH: 37
<212> TYPE: DNA
<213> ORGANISM: Artificial
<220> FEATURE:
<223> OTHER INFORMATION: primer

<400> SEQUENCE: 14 gggggggaagc ttggtgttac cactggtggc ttcgatt                              37

<210> SEQ ID NO 15
<211> LENGTH: 37
<212> TYPE: DNA
<213> ORGANISM: Artificial
<220> FEATURE:
<223> OTHER INFORMATION: primer

<400> SEQUENCE: 15 gggggggaagc ttaatattct gtggcgtcag ctccggc                              37

<210> SEQ ID NO 16
<211> LENGTH: 36
<212> TYPE: DNA
<213> ORGANISM: Artificial
<220> FEATURE:
<223> OTHER INFORMATION: primer

<400> SEQUENCE: 16
gcggcgggat ccatactgca tttgtcggca gcaaca                                36

<210> SEQ ID NO 17
<211> LENGTH: 25
<212> TYPE: DNA
<213> ORGANISM: Artificial
<220> FEATURE:
<223> OTHER INFORMATION: primer

<400> SEQUENCE: 17
aacccgcgat gaggaacttg ctctc                                            25

<210> SEQ ID NO 18
<211> LENGTH: 25
<212> TYPE: DNA
<213> ORGANISM: Artificial
<220> FEATURE:
<223> OTHER INFORMATION: primer

<400> SEQUENCE: 18
ttcaatgacc ttacggcgtt tcctc                                            25

<210> SEQ ID NO 19
<211> LENGTH: 37
<212> TYPE: DNA
<213> ORGANISM: Artificial
<220> FEATURE:
<223> OTHER INFORMATION: primer

<400> SEQUENCE: 19
cgccgcggat cccaatctac cggttatttt gataacc                               37

<210> SEQ ID NO 20
<211> LENGTH: 37
<212> TYPE: DNA
<213> ORGANISM: Artificial
<220> FEATURE:
<223> OTHER INFORMATION: primer
```

<400> SEQUENCE: 20
cggcggggta ccttttcggc atcccaaatc atgttgg                                37

<210> SEQ ID NO 21
<211> LENGTH: 37
<212> TYPE: DNA
<213> ORGANISM: Artificial
<220> FEATURE:
<223> OTHER INFORMATION: primer

<400> SEQUENCE: 21
gccgccggta ccattaaacc tggcccgcat aaaattc                                37

<210> SEQ ID NO 22
<211> LENGTH: 37
<212> TYPE: DNA
<213> ORGANISM: Artificial
<220> FEATURE:
<223> OTHER INFORMATION: primer

<400> SEQUENCE: 22
cgccgcggat cccaagctgg cattactgtt gcaattc                                37

<210> SEQ ID NO 23
<211> LENGTH: 24
<212> TYPE: DNA
<213> ORGANISM: Artificial
<220> FEATURE:
<223> OTHER INFORMATION: primer

<400> SEQUENCE: 23
ctatcgcgat aaacacgcga tgtg                                              24

<210> SEQ ID NO 24
<211> LENGTH: 23
<212> TYPE: DNA
<213> ORGANISM: Artificial
<220> FEATURE:
<223> OTHER INFORMATION: primer

<400> SEQUENCE: 24
ggcgaaagtt tgaagcaggc cac                                               23

<210> SEQ ID NO 25
<211> LENGTH: 28
<212> TYPE: DNA
<213> ORGANISM: Artificial
<220> FEATURE:
<223> OTHER INFORMATION: primer

<400> SEQUENCE: 25
atccagtcga tgatcgatac cgggatcc                                          28

<210> SEQ ID NO 26
<211> LENGTH: 26
<212> TYPE: DNA
<213> ORGANISM: Artificial
<220> FEATURE:
<223> OTHER INFORMATION: primer

<400> SEQUENCE: 26
ggcgctacga acaggaacag gaattc                                            26

<210> SEQ ID NO 27
<211> LENGTH: 35
<212> TYPE: DNA

<213> ORGANISM: Artificial
<220> FEATURE:
<223> OTHER INFORMATION: primer

<400> SEQUENCE: 27
ggccgaattc cgtcatggtg tgcgggttat ttccg                          35

<210> SEQ ID NO 28
<211> LENGTH: 35
<212> TYPE: DNA
<213> ORGANISM: Artificial
<220> FEATURE:
<223> OTHER INFORMATION: primer

<400> SEQUENCE: 28
cgcgggatcc ttaacgaaca gcgcggatgg cgtta                          35

<210> SEQ ID NO 29
<211> LENGTH: 25
<212> TYPE: DNA
<213> ORGANISM: Artificial
<220> FEATURE:
<223> OTHER INFORMATION: primer

<400> SEQUENCE: 29
ttctgaaagc caataacatc cagag                                     25

<210> SEQ ID NO 30
<211> LENGTH: 25
<212> TYPE: DNA
<213> ORGANISM: Artificial
<220> FEATURE:
<223> OTHER INFORMATION: primer

<400> SEQUENCE: 30
ggtaaaaatc cacgattgcg caacg                                     25

<210> SEQ ID NO 31
<211> LENGTH: 1134
<212> TYPE: DNA
<213> ORGANISM: Escherichia coli
<220> FEATURE:
<221> NAME/KEY: CDS
<222> LOCATION: (223)..(1044)
<223> OTHER INFORMATION:

<400> SEQUENCE: 31
tccgcgaact ggcgcatcgc ttcggcgttg aaatgccaat aaccgaggaa atttatcaag    60
tattatattg cggaaaaaac gcgcgcgagg cagcattgac tttactaggt cgtgcacgca   120
aggacgagcg cagcagccac taaccccagg gaacctttgt taccgctatg acccggcccg   180
cgcagaacgg gccggtcatt atctcatcgt gtggagtaag ca atg tcg tgt gaa      234
                                              Met Ser Cys Glu
                                                1 gaa ctg gaa att gtc tgg aac aat att aaa gcc gaa gcc aga acg ctg    282
Glu Leu Glu Ile Val Trp Asn Asn Ile Lys Ala Glu Ala Arg Thr Leu
 5              10                  15                  20 gcg gac tgt gag cca atg ctg gcc agt ttt tac cac gcg acg cta ctc    330
Ala Asp Cys Glu Pro Met Leu Ala Ser Phe Tyr His Ala Thr Leu Leu
             25                  30                  35 aag cac gaa aac ctt ggc agt gca ctg agc tac atg ctg gcg aac aag    378
Lys His Glu Asn Leu Gly Ser Ala Leu Ser Tyr Met Leu Ala Asn Lys
         40                  45                  50 ctg tca tcg cca att atg cct gct att gct atc cgt gaa gtg gtg gaa    426
Leu Ser Ser Pro Ile Met Pro Ala Ile Ala Ile Arg Glu Val Val Glu
     55                  60                  65

```
gaa gcc tac gcc gct gac ccg gaa atg atc gcc tct gcg gcc tgt gat       474
Glu Ala Tyr Ala Ala Asp Pro Glu Met Ile Ala Ser Ala Ala Cys Asp
    70                  75                  80 att cag gcg gtg cgt acc cgc gac ccg gca gtc gat aaa tac tca acc       522
Ile Gln Ala Val Arg Thr Arg Asp Pro Ala Val Asp Lys Tyr Ser Thr
85                  90                  95                 100 ccg ttg tta tac ctg aag ggt ttt cat gcc ttg cag gcc tat cgc atc       570
Pro Leu Leu Tyr Leu Lys Gly Phe His Ala Leu Gln Ala Tyr Arg Ile
                105                 110                 115 ggt cac tgg ttg tgg aat cag ggg cgt cgc gca ctg gca atc ttt ctg       618
Gly His Trp Leu Trp Asn Gln Gly Arg Arg Ala Leu Ala Ile Phe Leu
            120                 125                 130 caa aac cag gtt tct gtg acg ttc cag gtc gat att cac ccg gca gca       666
Gln Asn Gln Val Ser Val Thr Phe Gln Val Asp Ile His Pro Ala Ala
        135                 140                 145 aaa att ggt cgc ggt atc atg ctt gac cac gcg aca ggc atc gtc gtt       714
Lys Ile Gly Arg Gly Ile Met Leu Asp His Ala Thr Gly Ile Val Val
    150                 155                 160 ggt gaa acg gcg gtg att gaa aac gac gta tcg att ctg caa tct gtg       762
Gly Glu Thr Ala Val Ile Glu Asn Asp Val Ser Ile Leu Gln Ser Val
165                 170                 175                 180 acg ctt ggc ggt acg ggt aaa tct ggt ggt gac cgt cac ccg aaa att       810
Thr Leu Gly Gly Thr Gly Lys Ser Gly Gly Asp Arg His Pro Lys Ile
                185                 190                 195 cgt gaa ggt gtg atg att ggc gcg ggc gcg aaa atc ctc ggc aat att       858
Arg Glu Gly Val Met Ile Gly Ala Gly Ala Lys Ile Leu Gly Asn Ile
            200                 205                 210 gaa gtt ggg cgc ggc gcg aag att ggc gca ggt tcc gtg gtg ctg caa       906
Glu Val Gly Arg Gly Ala Lys Ile Gly Ala Gly Ser Val Val Leu Gln
        215                 220                 225 ccg gtg ccg ccg cat acc acc gcc gct ggc gtt ccg gct cgt att gtc       954
Pro Val Pro Pro His Thr Thr Ala Ala Gly Val Pro Ala Arg Ile Val
    230                 235                 240 ggt aaa cca gac agc gat aag cca tca atg gat atg gac cag cat ttc      1002
Gly Lys Pro Asp Ser Asp Lys Pro Ser Met Asp Met Asp Gln His Phe
245                 250                 255                 260 aac ggt att aac cat aca ttt gag tat ggg gat ggg atc taa              1044
Asn Gly Ile Asn His Thr Phe Glu Tyr Gly Asp Gly Ile
                265                 270 tgtcctgtga tcgtgccgga tgcgatgtaa tcatctatcc ggcctacagt aactaatctc    1104
tcaataccgc tcccgatacc ccaactgtcg                                     1134

<210> SEQ ID NO 32
<211> LENGTH: 273
<212> TYPE: PRT
<213> ORGANISM: Escherichia coli

<400> SEQUENCE: 32

Met Ser Cys Glu Glu Leu Glu Ile Val Trp Asn Asn Ile Lys Ala Glu
1               5                   10                  15

Ala Arg Thr Leu Ala Asp Cys Glu Pro Met Leu Ala Ser Phe Tyr His
                20                  25                  30

Ala Thr Leu Leu Lys His Glu Asn Leu Gly Ser Ala Leu Ser Tyr Met
            35                  40                  45

Leu Ala Asn Lys Leu Ser Ser Pro Ile Met Pro Ala Ile Ala Ile Arg
        50                  55                  60

Glu Val Val Glu Glu Ala Tyr Ala Ala Asp Pro Glu Met Ile Ala Ser
65                  70                  75                  80
```

```
Ala Ala Cys Asp Ile Gln Ala Val Arg Thr Arg Asp Pro Ala Val Asp
            85                  90                  95

Lys Tyr Ser Thr Pro Leu Leu Tyr Leu Lys Gly Phe His Ala Leu Gln
        100                 105                 110

Ala Tyr Arg Ile Gly His Trp Leu Trp Asn Gln Gly Arg Arg Ala Leu
            115                 120                 125

Ala Ile Phe Leu Gln Asn Gln Val Ser Val Thr Phe Gln Val Asp Ile
130                 135                 140

His Pro Ala Ala Lys Ile Gly Arg Gly Ile Met Leu Asp His Ala Thr
145                 150                 155                 160

Gly Ile Val Val Gly Glu Thr Ala Val Ile Glu Asn Asp Val Ser Ile
                165                 170                 175

Leu Gln Ser Val Thr Leu Gly Gly Thr Gly Lys Ser Gly Gly Asp Arg
            180                 185                 190

His Pro Lys Ile Arg Glu Gly Val Met Ile Gly Ala Gly Ala Lys Ile
        195                 200                 205

Leu Gly Asn Ile Glu Val Gly Arg Gly Ala Lys Ile Gly Ala Gly Ser
210                 215                 220

Val Val Leu Gln Pro Val Pro Pro His Thr Thr Ala Ala Gly Val Pro
225                 230                 235                 240

Ala Arg Ile Val Gly Lys Pro Asp Ser Asp Lys Pro Ser Met Asp Met
                245                 250                 255

Asp Gln His Phe Asn Gly Ile Asn His Thr Phe Glu Tyr Gly Asp Gly
            260                 265                 270

Ile

<210> SEQ ID NO 33
<211> LENGTH: 912
<212> TYPE: DNA
<213> ORGANISM: Escherichia coli
<220> FEATURE:
<221> NAME/KEY: CDS
<222> LOCATION: (1)..(912)
<223> OTHER INFORMATION:

<400> SEQUENCE: 33 gtg agt aca tta gaa caa aca ata ggc aat acg cct ctg gtg aag ttg    48
Val Ser Thr Leu Glu Gln Thr Ile Gly Asn Thr Pro Leu Val Lys Leu
1               5                   10                  15 cag cga atg ggg ccg gat aac ggc agt gaa gtg tgg tta aaa ctg gaa    96
Gln Arg Met Gly Pro Asp Asn Gly Ser Glu Val Trp Leu Lys Leu Glu
            20                  25                  30 ggc aat aac ccg gca ggt tcg gtg aaa gat cgt gcg gca ctt tcg atg   144
Gly Asn Asn Pro Ala Gly Ser Val Lys Asp Arg Ala Ala Leu Ser Met
        35                  40                  45 atc gtc gag gcg gaa aag cgc ggg gaa att aaa ccg ggt gat gtc tta   192
Ile Val Glu Ala Glu Lys Arg Gly Glu Ile Lys Pro Gly Asp Val Leu
50                  55                  60 atc gaa gcc acc agt ggt aac acc ggc att gcg ctg gca atg att gcc   240
Ile Glu Ala Thr Ser Gly Asn Thr Gly Ile Ala Leu Ala Met Ile Ala
65                  70                  75                  80 gcg ctg aaa ggc tat cgc atg aaa ttg ctg atg ccc gac aac atg agc   288
Ala Leu Lys Gly Tyr Arg Met Lys Leu Leu Met Pro Asp Asn Met Ser
                85                  90                  95 cag gaa cgc cgt gcg gcg atg cgt gct tat ggt gcg gaa ctg att ctt   336
Gln Glu Arg Arg Ala Ala Met Arg Ala Tyr Gly Ala Glu Leu Ile Leu
            100                 105                 110 gtc acc aaa gag cag ggc atg gaa ggt gcg cgc gat ctg gcg ctg gag   384
```

```
                Val Thr Lys Glu Gln Gly Met Glu Gly Ala Arg Asp Leu Ala Leu Glu
                    115                 120                 125 atg gcg aat cgt ggc gaa gga aag ctg ctc gat cag ttc aat aat ccc         432
Met Ala Asn Arg Gly Glu Gly Lys Leu Leu Asp Gln Phe Asn Asn Pro
    130                 135                 140 gat aac cct tat gcg cat tac acc acc act ggg ccg gaa atc tgg cag         480
Asp Asn Pro Tyr Ala His Tyr Thr Thr Thr Gly Pro Glu Ile Trp Gln
145                 150                 155                 160 caa acc ggc ggg cgc atc act cat ttt gtc tcc agc atg ggg acg acc         528
Gln Thr Gly Gly Arg Ile Thr His Phe Val Ser Ser Met Gly Thr Thr
                165                 170                 175 ggc act atc acc ggc gtc tca cgc ttt atg cgc gaa caa tcc aaa ccg         576
Gly Thr Ile Thr Gly Val Ser Arg Phe Met Arg Glu Gln Ser Lys Pro
            180                 185                 190 gtg acc att gtc ggc ctg caa ccg gaa gag ggc agc agc att ccc ggc         624
Val Thr Ile Val Gly Leu Gln Pro Glu Glu Gly Ser Ser Ile Pro Gly
        195                 200                 205 att cgc cgc tgg cct acg gaa tat ctg ccg ggg att ttc aac gct tct         672
Ile Arg Arg Trp Pro Thr Glu Tyr Leu Pro Gly Ile Phe Asn Ala Ser
    210                 215                 220 ctg gtg gat gag gtg ctg gat att cat cag cgc gat gcg gaa aac acc         720
Leu Val Asp Glu Val Leu Asp Ile His Gln Arg Asp Ala Glu Asn Thr
225                 230                 235                 240 atg cgc gaa ctg gcg gtg cgg gaa gga ata ttc tgt ggc gtc agc tcc         768
Met Arg Glu Leu Ala Val Arg Glu Gly Ile Phe Cys Gly Val Ser Ser
                245                 250                 255 ggc ggc gcg gtt gcc gga gca ctg cgg gtg gca aaa gct aac cct gac         816
Gly Gly Ala Val Ala Gly Ala Leu Arg Val Ala Lys Ala Asn Pro Asp
            260                 265                 270 gcg gtg gtg gtg gcg atc atc tgc gat cgt ggc gat cgc tac ctt tct         864
Ala Val Val Val Ala Ile Ile Cys Asp Arg Gly Asp Arg Tyr Leu Ser
        275                 280                 285 acc ggg gtg ttt ggg gaa gag cat ttt agc cag ggg gcg ggg att taa         912
Thr Gly Val Phe Gly Glu Glu His Phe Ser Gln Gly Ala Gly Ile
    290                 295                 300

<210> SEQ ID NO 34
<211> LENGTH: 303
<212> TYPE: PRT
<213> ORGANISM: Escherichia coli

<400> SEQUENCE: 34

Val Ser Thr Leu Glu Gln Thr Ile Gly Asn Thr Pro Leu Val Lys Leu
1               5                   10                  15

Gln Arg Met Gly Pro Asp Asn Gly Ser Glu Val Trp Leu Lys Leu Glu
                20                  25                  30

Gly Asn Asn Pro Ala Gly Ser Val Lys Asp Arg Ala Ala Leu Ser Met
            35                  40                  45

Ile Val Glu Ala Glu Lys Arg Gly Glu Ile Lys Pro Gly Asp Val Leu
        50                  55                  60

Ile Glu Ala Thr Ser Gly Asn Thr Gly Ile Ala Leu Ala Met Ile Ala
65                  70                  75                  80

Ala Leu Lys Gly Tyr Arg Met Lys Leu Leu Met Pro Asp Asn Met Ser
                85                  90                  95

Gln Glu Arg Arg Ala Ala Met Arg Ala Tyr Gly Ala Glu Leu Ile Leu
            100                 105                 110

Val Thr Lys Glu Gln Gly Met Glu Gly Ala Arg Asp Leu Ala Leu Glu
        115                 120                 125

Met Ala Asn Arg Gly Glu Gly Lys Leu Leu Asp Gln Phe Asn Asn Pro
```

```
                   130                 135                 140
Asp Asn Pro Tyr Ala His Tyr Thr Thr Thr Gly Pro Glu Ile Trp Gln
145                 150                 155                 160

Gln Thr Gly Gly Arg Ile Thr His Phe Val Ser Ser Met Gly Thr Thr
                165                 170                 175

Gly Thr Ile Thr Gly Val Ser Arg Phe Met Arg Glu Gln Ser Lys Pro
                180                 185                 190

Val Thr Ile Val Gly Leu Gln Pro Glu Glu Gly Ser Ser Ile Pro Gly
                195                 200                 205

Ile Arg Arg Trp Pro Thr Glu Tyr Leu Pro Gly Ile Phe Asn Ala Ser
    210                 215                 220

Leu Val Asp Glu Val Leu Asp Ile His Gln Arg Asp Ala Glu Asn Thr
225                 230                 235                 240

Met Arg Glu Leu Ala Val Arg Glu Gly Ile Phe Cys Gly Val Ser Ser
                245                 250                 255

Gly Gly Ala Val Ala Gly Ala Leu Arg Val Ala Lys Ala Asn Pro Asp
                260                 265                 270

Ala Val Val Val Ala Ile Ile Cys Asp Arg Gly Asp Arg Tyr Leu Ser
                275                 280                 285

Thr Gly Val Phe Gly Glu Glu His Phe Ser Gln Gly Ala Gly Ile
                290                 295                 300

<210> SEQ ID NO 35
<211> LENGTH: 1173
<212> TYPE: DNA
<213> ORGANISM: Escherichia coli
<220> FEATURE:
<221> NAME/KEY: CDS
<222> LOCATION: (1)..(1173)
<223> OTHER INFORMATION:

<400> SEQUENCE: 35 atg ttc gat ttt tca aag gtc gtg gat cgt cat ggc aca tgg tgt aca        48
Met Phe Asp Phe Ser Lys Val Val Asp Arg His Gly Thr Trp Cys Thr
1               5                   10                  15 cag tgg gat tat gtc gct gac cgt ttc ggc act gct gac ctg tta ccg        96
Gln Trp Asp Tyr Val Ala Asp Arg Phe Gly Thr Ala Asp Leu Leu Pro
            20                  25                  30 ttc acg att tca gac atg gat ttt gcc act gcc ccc tgc att atc gag       144
Phe Thr Ile Ser Asp Met Asp Phe Ala Thr Ala Pro Cys Ile Ile Glu
        35                  40                  45 gcg ctg aat cag cgc ctg atg cac ggc gta ttt ggc tac agc cgc tgg       192
Ala Leu Asn Gln Arg Leu Met His Gly Val Phe Gly Tyr Ser Arg Trp
    50                  55                  60 aaa aac gat gag ttt ctc gcg gct att gcc cac tgg ttt tcc acc cag       240
Lys Asn Asp Glu Phe Leu Ala Ala Ile Ala His Trp Phe Ser Thr Gln
65                  70                  75                  80 cat tac acc gcc atc gat tct cag acg gtg gtg tat ggc cct tct gtc       288
His Tyr Thr Ala Ile Asp Ser Gln Thr Val Val Tyr Gly Pro Ser Val
                85                  90                  95 atc tat atg gtt tca gaa ctg att cgt cag tgg tct gaa aca ggt gaa       336
Ile Tyr Met Val Ser Glu Leu Ile Arg Gln Trp Ser Glu Thr Gly Glu
            100                 105                 110 ggc gtg gtg atc cac aca ccc gcc tat gac gca ttt tac aag gcc att       384
Gly Val Val Ile His Thr Pro Ala Tyr Asp Ala Phe Tyr Lys Ala Ile
        115                 120                 125 gaa ggt aac cag cgc aca gta atg ccc gtt gct tta gag aag cag gct       432
Glu Gly Asn Gln Arg Thr Val Met Pro Val Ala Leu Glu Lys Gln Ala
    130                 135                 140
```

```
gat ggt tgg ttt tgc gat atg ggc aag ttg gaa gcc gtg ttg gcg aaa    480
Asp Gly Trp Phe Cys Asp Met Gly Lys Leu Glu Ala Val Leu Ala Lys
145                 150                 155                 160 cca gaa tgt aaa att atg ctc ctg tgt agc cca cag aat cct acc ggg    528
Pro Glu Cys Lys Ile Met Leu Leu Cys Ser Pro Gln Asn Pro Thr Gly
                165                 170                 175 aaa gtg tgg acg tgc gat gag ctg gag atc atg gct gac ctg tgc gag    576
Lys Val Trp Thr Cys Asp Glu Leu Glu Ile Met Ala Asp Leu Cys Glu
            180                 185                 190 cgt cat ggt gtg cgg gtt att tcc gat gaa atc cat atg gat atg gtt    624
Arg His Gly Val Arg Val Ile Ser Asp Glu Ile His Met Asp Met Val
        195                 200                 205 tgg ggc gag cag ccg cat att ccc tgg agt aat gtg gct cgc gga gac    672
Trp Gly Glu Gln Pro His Ile Pro Trp Ser Asn Val Ala Arg Gly Asp
    210                 215                 220 tgg gcg ttg cta acg tcg ggc tcg aaa agt ttc aat att ccc gcc ctg    720
Trp Ala Leu Leu Thr Ser Gly Ser Lys Ser Phe Asn Ile Pro Ala Leu
225                 230                 235                 240 acc ggt gct tac ggg att ata gaa aat agc agt agc cgc gat gcc tat    768
Thr Gly Ala Tyr Gly Ile Ile Glu Asn Ser Ser Ser Arg Asp Ala Tyr
                245                 250                 255 tta tcg gca ctg aaa ggc cgt gat ggg ctt tct tcc cct tcg gta ctg    816
Leu Ser Ala Leu Lys Gly Arg Asp Gly Leu Ser Ser Pro Ser Val Leu
            260                 265                 270 gcg tta act gcc cat atc gcc gcc tat cag caa ggc gcg ccg tgg ctg    864
Ala Leu Thr Ala His Ile Ala Ala Tyr Gln Gln Gly Ala Pro Trp Leu
        275                 280                 285 gat gcc tta cgc atc tat ctg aaa gat aac ctg acg tat atc gca gat    912
Asp Ala Leu Arg Ile Tyr Leu Lys Asp Asn Leu Thr Tyr Ile Ala Asp
    290                 295                 300 aaa atg aac gcc gcg ttt cct gaa ctc aac tgg cag atc cca caa tcc    960
Lys Met Asn Ala Ala Phe Pro Glu Leu Asn Trp Gln Ile Pro Gln Ser
305                 310                 315                 320 act tat ctg gca tgg ctt gat tta cgt ccg ttg aat att gac gac aac   1008
Thr Tyr Leu Ala Trp Leu Asp Leu Arg Pro Leu Asn Ile Asp Asp Asn
                325                 330                 335 gcg ttg caa aaa gca ctt atc gaa caa gaa aaa gtc gcg atc atg ccg   1056
Ala Leu Gln Lys Ala Leu Ile Glu Gln Glu Lys Val Ala Ile Met Pro
            340                 345                 350 ggg tat acc tac ggt gaa gaa ggt cgt ggt ttt gtc cgt ctc aat gcc   1104
Gly Tyr Thr Tyr Gly Glu Glu Gly Arg Gly Phe Val Arg Leu Asn Ala
        355                 360                 365 ggc tgc cca cgt tcg aaa ctg gaa aaa ggt gtg gct gga tta att aac   1152
Gly Cys Pro Arg Ser Lys Leu Glu Lys Gly Val Ala Gly Leu Ile Asn
    370                 375                 380 gcc atc cgc gct gtt cgt taa                                       1173
Ala Ile Arg Ala Val Arg
385                 390

<210> SEQ ID NO 36
<211> LENGTH: 390
<212> TYPE: PRT
<213> ORGANISM: Escherichia coli

<400> SEQUENCE: 36

Met Phe Asp Phe Ser Lys Val Val Asp Arg His Gly Thr Trp Cys Thr
1               5                   10                  15

Gln Trp Asp Tyr Val Ala Asp Arg Phe Gly Thr Ala Asp Leu Leu Pro
            20                  25                  30

Phe Thr Ile Ser Asp Met Asp Phe Ala Thr Ala Pro Cys Ile Ile Glu
        35                  40                  45
```

-continued

Ala Leu Asn Gln Arg Leu Met His Gly Val Phe Gly Tyr Ser Arg Trp
    50                  55                  60

Lys Asn Asp Glu Phe Leu Ala Ile Ala His Trp Phe Ser Thr Gln
65                  70                  75                  80

His Tyr Thr Ala Ile Asp Ser Gln Thr Val Val Tyr Gly Pro Ser Val
                85                  90                  95

Ile Tyr Met Val Ser Glu Leu Ile Arg Gln Trp Ser Glu Thr Gly Glu
            100                 105                 110

Gly Val Val Ile His Thr Pro Ala Tyr Asp Ala Phe Tyr Lys Ala Ile
                115                 120                 125

Glu Gly Asn Gln Arg Thr Val Met Pro Val Ala Leu Glu Lys Gln Ala
            130                 135                 140

Asp Gly Trp Phe Cys Asp Met Gly Lys Leu Glu Ala Val Leu Ala Lys
145                 150                 155                 160

Pro Glu Cys Lys Ile Met Leu Leu Cys Ser Pro Gln Asn Pro Thr Gly
                165                 170                 175

Lys Val Trp Thr Cys Asp Glu Leu Glu Ile Met Ala Asp Leu Cys Glu
            180                 185                 190

Arg His Gly Val Arg Val Ile Ser Asp Glu Ile His Met Asp Met Val
            195                 200                 205

Trp Gly Glu Gln Pro His Ile Pro Trp Ser Asn Val Ala Arg Gly Asp
210                 215                 220

Trp Ala Leu Leu Thr Ser Gly Ser Lys Ser Phe Asn Ile Pro Ala Leu
225                 230                 235                 240

Thr Gly Ala Tyr Gly Ile Ile Glu Asn Ser Ser Ser Arg Asp Ala Tyr
                245                 250                 255

Leu Ser Ala Leu Lys Gly Arg Asp Gly Leu Ser Ser Pro Ser Val Leu
            260                 265                 270

Ala Leu Thr Ala His Ile Ala Ala Tyr Gln Gln Gly Ala Pro Trp Leu
            275                 280                 285

Asp Ala Leu Arg Ile Tyr Leu Lys Asp Asn Leu Thr Tyr Ile Ala Asp
        290                 295                 300

Lys Met Asn Ala Ala Phe Pro Glu Leu Asn Trp Gln Ile Pro Gln Ser
305                 310                 315                 320

Thr Tyr Leu Ala Trp Leu Asp Leu Arg Pro Leu Asn Ile Asp Asp Asn
                325                 330                 335

Ala Leu Gln Lys Ala Leu Ile Glu Gln Glu Lys Val Ala Ile Met Pro
            340                 345                 350

Gly Tyr Thr Tyr Gly Glu Glu Gly Arg Gly Phe Val Arg Leu Asn Ala
            355                 360                 365

Gly Cys Pro Arg Ser Lys Leu Glu Lys Gly Val Ala Gly Leu Ile Asn
        370                 375                 380

Ala Ile Arg Ala Val Arg
385                 390

L-CYSTEINE PRODUCING MICROORGANISM AND A METHOD FOR PRODUCING L-CYSTEINE

This application is a divisional under 35 U.S.C. §120 of U.S. patent application Ser. No. 11/070,084, filed Mar. 3, 2005, now abandoned, which claims priority under 35 U.S.C. §119 to Japanese Patent Application No. 2004-060483, filed on Mar. 4, 2004, which are incorporated in their entireties by reference. The Sequence Listing in electronic format filed herewith is also hereby incorporated by reference in its entirety (File Name: US-214D_Seq_List; File Size: 28 KB; Date Created: Dec. 10, 2009).

BACKGROUND OF THE INVENTION

1. Technical Field

The present invention relates to a method for producing L-cysteine, and a microorganism suitable for the production of L-cysteine. L-cysteine and derivatives thereof are used in the fields of pharmaceuticals, cosmetics, foods and the like.

2. Background Art

L-cysteine is conventionally obtained by extraction from keratin-containing substances such as hair, horns, and feathers, or by conversion of precursor DL-2-aminothiazoline-4-carboxylic acid using a microbial enzyme. Large scale production of L-cysteine has been attempted using an immobilized enzyme method with a novel enzyme.

Furthermore, production of L-cysteine has also been attempted by fermentation utilizing a microorganism. A method of producing L-cysteine using a microorganism has been reported, wherein said microorganism contains a DNA encoding serine acetyltransferase (SAT) with a mutation which prevents feedback inhibition by L-cysteine (WO 97/15673). A method of producing L-cysteine using a strain of *Escherichia coli* which contains a gene encoding SAT isozyme of *Arabidopsis thaliana* is disclosed in FEMS Microbiol. Lett., vol. 179 (1999) p 453-459. This SAT isozyme gene is resistant to feedback inhibition by L-cysteine. Also, a method of producing L-cysteine using a microorganism which overexpresses a gene encoding a protein that excretes an antibiotic or a toxic substance is disclosed in JP11-56381A.

Furthermore, the inventors of the present invention have disclosed a method of producing L-cysteine using a strain of *Escherichia coli* which contains serine acetyltransferase with reduced feedback inhibition by L-cysteine, and in which the L-cysteine-decomposing system is attenuated (JP11-155571A). The L-cysteine-decomposing system of the bacterium is attenuated by reduction of the intracellular activity of cysteine desulfhydrase (hereinafter, also referred to as "CD").

Enzymes which have been reported to have CD activity in *Escherichia coli* include cystathionine-β-lyase (metC gene product, hereinafter, also referred to as "CBL") (Chandra et. al., Biochemistry, vol. 21 (1982) p 3064-3069) and tryptophanase (tnaA gene product, hereinafter, also referred to as "TNase") (Austin Newton, et al., J. Biol. Chem. vol. 240 (1965) p 1211-1218). A method of producing L-cysteine using an *Escherichia coli* strain which has reduced activities of cystathionine-(3-lyase and tryptophanase is disclosed in JP2003-169668A (EP1,298,200). However, no enzymes other than these have been previously reported to have CD activity.

SUMMARY OF THE INVENTION

An object of the present invention is to identify a gene encoding a protein having CD activity, and utilize the gene for breeding L-cysteine-producing microorganism.

In order to attain the above-mentioned object, the inventors of the present invention made extensive studies and as a result, have found that the enzymes O-acetylserine sulphydrylase B (OASS-B) and MalY regulatory protein (MalY) have CD activity in *Escherichia coli*. The inventors also found that reducing CD activity by modifying these genes leads to improvement in the production of L-cysteine.

It is an object of the present invention to provide an *Escherichia* bacterium having L-cysteine-producing ability, wherein said bacterium contains a gene encoding O-acetylserine sulphydrylase B, and wherein said gene is modified so that cysteine desulfhydrase activity is reduced or eliminated.

It is a further object of the present invention to provide an *Escherichia* bacterium having L-cysteine-producing ability, wherein said bacterium contains a gene encoding MalY regulatory protein, and wherein said gene is modified so that cysteine desulfhydrase activity is reduced or eliminated.

It is a further object of the present invention to provide an *Escherichia* bacterium as described above, wherein said gene encoding O-acetylserine sulphydrylase B is disrupted.

It is a further object of the present invention to provide an *Escherichia* bacterium as described above, wherein said gene encoding MalY regulatory protein is disrupted.

It is a further object of the present invention to provide an *Escherichia* bacterium as described above, wherein activity of an L-cysteine biosynthetic enzyme is enhanced.

It is a further object of the present invention to provide an *Escherichia* bacterium as described above, wherein said L-cysteine biosynthetic enzyme is serine acetyltransferase.

It is a further object of the present invention to provide an *Escherichia* bacterium as described above, wherein said serine acetyltransferase is resistant to feedback inhibition by L-cysteine.

It is a further object of the present invention to provide an *Escherichia* bacterium as described above, wherein said *Escherichia* bacterium is *Escherichia coli*.

It is a further object of the present invention to provide a method of producing L-cysteine comprising culturing the *Escherichia* bacterium as described above in a medium, and collecting L-cysteine from the medium.

BRIEF DESCRIPTION OF THE DRAWINGS

FIG. 2 shows primers used in gene disruption.

DETAILED DESCRIPTION OF THE PREFERRED EMBODIMENTS

Figure 1:
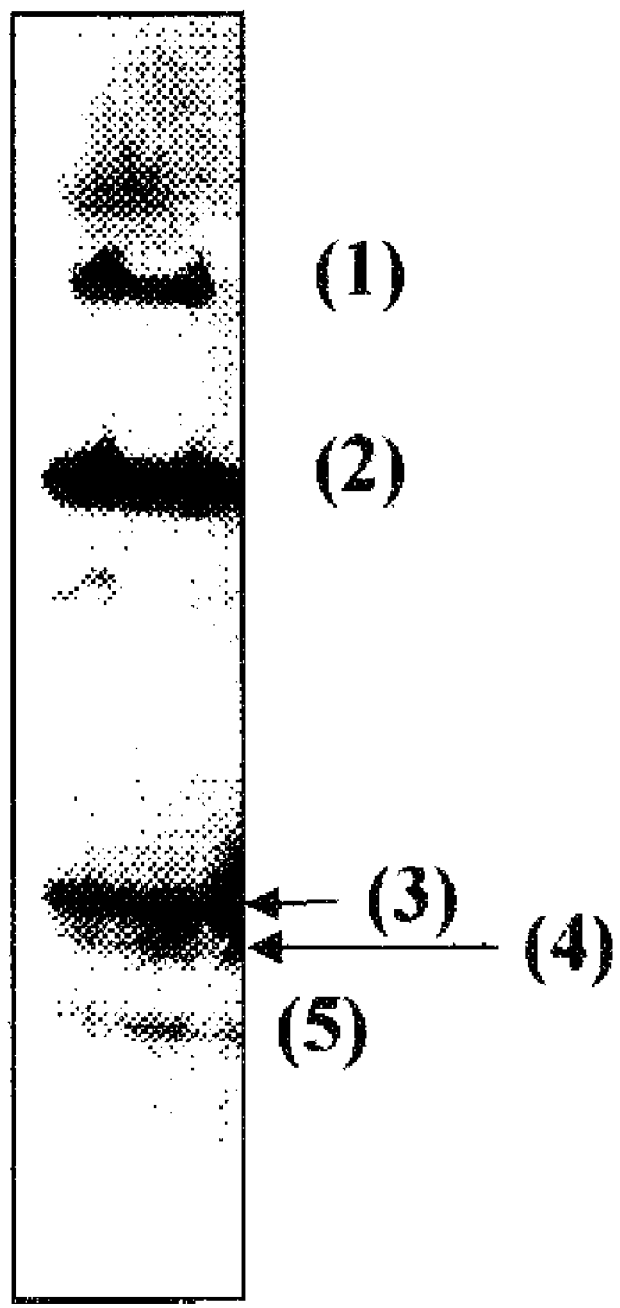
FIG. 1 shows the results of CD activity staining of *Escherichia coli* cell extracts on Native-PAGE.

Hereinafter, the present invention will be explained in detail. In the present invention, unless otherwise described, L-cysteine refers to a reduced-type of L-cysteine, L-cystine, or a mixture thereof.

The *Escherichia* bacterium of the present invention has L-cysteine-producing ability and contains a gene encoding O-acetylserine sulphydrylase B (OASS-B) or MalY regulatory protein, wherein the gene is modified so that the cysteine desulfhydrase (CD) activity of the bacterium is reduced or eliminated. The *Escherichia* bacterium of the present invention may have L-cysteine producing-ability and may contain both of the genes encoding OASS-B and MalY regulatory protein which are modified so that the CD activity of the bacterium is reduced or eliminated. In the *Escherichia* bacterium of the present invention, one or both of the genes encoding tryptophanase (TNase) and cystathionine-β-lyase (CBL) may also be modified so that the CD activity of the bacterium is further reduced.

The term "L-cysteine-producing ability" as used herein refers to an ability of the *Escherichia* bacterium of the present invention to cause accumulation of L-cysteine in a culture medium to such a degree that L-cysteine can be collected from the medium when the bacterium is cultured in the medium. The L-cysteine-producing ability may be imparted to a parent strain of an *Escherichia* bacterium by a mutation technique or a recombinant DNA technique. The recombinant DNA technique includes introduction of a gene encoding an L-cysteine biosynthetic enzyme. Alternatively, bacteria having native L-cysteine-producing ability may also be used. Furthermore, a bacterium imparted with an L-cysteine-producing ability by modification of a gene encoding O-acetylserine sulphydrylase B (OASS-B) or MalY regulatory protein may be used.

The *Escherichia* bacteria which can be used as a parent strain include those described in Neidhardt, F. C. et al. (*Escherichia coli* and *Salmonella Typhimurium*, American Society for Microbiology, Washington D.C., 1208, table 1), and *Escherichia coli* is preferably used. Wild-type strains of *Escherichia coli* include K12 strain, or mutants thereof such as *Escherichia coli* MG1655 strain (ATCC No. 47076) and W3110 strain (ATCC No. 27325). These bacteria strains can be obtained from the American Type Culture Collection (ATCC, Address: P.O. Box 1549, Manassas, Va. 20108, United States of America).

The *Escherichia* bacteria of the present invention can be obtained by modifying a gene encoding OASS-B or MalY regulatory protein in a parent strain so that CD activity of the strain is reduced or eliminated, and then imparting an L-cysteine-producing ability to the modified strain. The bacteria of the present invention can also be obtained by imparting an L-cysteine-producing ability to a parent strain, and then modifying a gene encoding OASS-B or MalY regulatory protein so that CD activity of the strain is reduced or eliminated. One or both of the genes encoding TNase and CBL may be further modified.

The method of obtaining the *Escherichia* bacteria of the present invention will be explained in detail.

<1> Modification of a Gene Encoding OASS-B or MalY Regulatory Protein

Examples of the methods of modifying a gene encoding OASS-B or MalY regulatory protein so that the CD activity of the *Escherichia* bacteria is reduced or eliminated include a mutation treatment method and a gene disruption method. Examples of the mutation treatment method include treating *Escherichia* bacteria with ultraviolet ray irradiation or with a mutagen used in ordinary mutation treatments, such as N-methyl-N'-nitro-N-nitrosoguanidine (NTG) or nitrous acid, and selecting mutants which contain a mutation reducing the CD activity in a gene encoding OASS-B or MalY regulatory protein. To reduce or eliminate the CD activity of OASS-B or MalY regulatory protein with high accuracy, it is preferable to disrupt a gene encoding OASS-B or MalY regulatory protein.

In *Escherichia coli*, OASS-B is encoded by the cysM gene, and MalY regulatory protein is encoded by the malY gene. The nucleotide sequences of these genes have been already reported (see for cysM; GenBank accession M32101 (SEQ ID NO: 33), J. Bacteriol. 172 (6), 3351-3357 (1990), and for malY; GenBank accession M60722 (SEQ ID NO: 35), J. Bacteriol. 173 (15), 4862-4876 (1991)). Accordingly, DNA fragments which can be used to disrupt the genes can be obtained by PCR using primers based on the nucleotide sequences from a chromosomal DNA of *Escherichia coli*. More specifically, the cysM gene deletion mutant (deletion-type cysM gene) and the malY gene deletion mutant (deletion-type malY gene) can be obtained by PCR using the primers shown in FIG. 2. DNA fragments for gene disruption are not limited to those derived from *Escherichia coli*, and may be DNAs derived from other organisms or synthetic DNAs as long as they can cause homologous recombination with a chromosomal DNA of a host bacterium. For example, DNAs having 80% or more, preferably 90% or more, more preferably 95% or more homology to the cysM gene or malY gene of *Escherichia coli* may be used. Homology of the DNA sequences can be determined using the algorithm BLAST (Pro. Natl. Acad. Sci. USA, 90, and 5873 (1993)) and FASTA (Methods Enzymol., 183, and 63 (1990)) by Karlin and Altschul. The BLASTN and BLASTX programs have been developed based on this algorithm BLAST. (refer to http://www.ncbi.nlm.nih.gov). Furthermore, DNAs able to hybridize with the cysM gene or malY gene of *Escherichia coli* under stringent conditions may also be used. "Stringent conditions" as used herein are conditions under which a so-called specific hybrid is formed, and a non-specific hybrid is not formed. It is difficult to clearly express this condition by using any numerical value. However, examples of stringent conditions include, those under which DNAs having high homology to each other, for example, DNAs having a homology of not less than 50%, hybridize to each other, and DNAs having homology lower than 50% do not hybridize to each other, and those under which DNAs hybridize to each other at a salt concentration with washing typical of Southern hybridization, i.e., washing once or preferably 2-3 times under 1×SSC, 0.1% SDS at 60° C., preferably 0.1×SSC, 0.1% SDS at 60° C., more preferably 0.1×SSC, 0.1% SDS at 68° C.

Hereinafter, a method of disrupting the gene encoding OASS-B will be explained. The gene encoding MalY regulatory protein can be disrupted or mutated in a similar manner.

A chromosomal cysM gene can be disrupted by transforming an *Escherichia* bacterium with a DNA containing a cysM gene which has part of its sequence deleted, and subsequent loss of normal OASS-B protein function (deletion-type cysM gene), and causing recombination between the deletion-type cysM gene and the chromosomal cysM gene. Examples of the deletion-type cysM gene used in transformation include genes having part of a sequence of the cysM gene deleted, genes having an corresponding expression regulatory region such as a promoter deleted or mutated so that of the expression of the cysM gene decreases, and genes into which a site-specific mutation is introduced so that the CD activity of a protein encoded by the cysM gene decreases.

The gene disruption technique using homologous recombination has already been established and examples thereof include using a linear DNA or a plasmid containing a temperature-sensitive replication origin. Examples of plasmids containing a temperature-sensitive replication origin for *Escherichia coli* include pMAN031 (Yasueda, H. et al., Appl. Microbiol. Biotechnol., 36, 211 (1991)), pMAN997 (WO 99/03988), and pEL3 (K. A. Armstrong, et al., J. Mol. Biol. (1984) 175, 331-347).

A cysM gene on a host chromosome can be replaced with the deletion-type cysM gene, for example, as follows. That is, a recombinant DNA is prepared by inserting into a vector a temperature-sensitive replication origin, a deletion-type cysM gene, and a marker gene conferring resistance to a drug such as ampicillin or chloramphenicol. Then, an *Escherichia* bacterium is transformed with the recombinant DNA. Furthermore, the transformant strain is cultured at a temperature at which the temperature-sensitive replication origin does not function. Then the transformant strain is cultured in a medium containing the drug to obtain the transformant strain in which the recombinant DNA is incorporated into the chromosomal DNA.

In the strain in which the recombinant DNA is incorporated into the chromosomal DNA as described above, the deletion-type cysM gene is recombined with the native cysM, and the two fusion genes of the chromosomal cysM gene and the deletion-type cysM gene are inserted into the chromosome so that the other portions of the recombinant DNA (vector segment, temperature-sensitive replication origin and drug resistance marker) are present between the two fusion genes. Therefore, the transformant strain expresses normal OASS-B because the normal cysM gene is dominant in this state.

Then, in order to leave only the deletion-type cysM gene on the chromosomal DNA, one copy of the cysM gene is eliminated along with the vector segment (including the temperature-sensitive replication origin and the drug resistance marker) from the chromosomal DNA by recombination of two of the cysM genes. In this case, the normal cysM gene is left on the chromosomal DNA and the deletion-type cysM gene is excised from the chromosomal DNA, or to the contrary, the deletion-type cysM gene is left on the chromosomal DNA and the normal cysM gene is excised from the chromosomal DNA. In both cases, the excised DNA may be harbored in the cell as a plasmid when the cell is cultured at a temperature which allows the temperature-sensitive replication origin to function. Subsequently, if the cell is cultured at a temperature which does not allow the temperature-sensitive replication origin to function, the cysM gene on the plasmid is eliminated with the plasmid from the cell. Then, a strain having the disrupted cysM gene left in the chromosome can be selected by PCR, Southern hybridization, or the like.

CD activity is reduced or eliminated in the cysM gene-disrupted strain or mutant strain obtained as described above. Reduction or elimination of the CD activity in the cysM gene-disrupted strain or mutant strain can be confirmed by measuring the CD activity of a cell extract of a candidate strain by CD activity staining or quantification of hydrogen sulfide as described in the Examples, and comparing it with the CD activity of the parent or non-modified strain.

The bacteria of the present invention may be strains in which one or both of the genes encoding tryptophanase (TNase) and cystathionine-β-lyase (CBL) are modified so that CD activity of the strain is further reduced. The method of modifying those genes (tnaA gene or metC gene) is disclosed in detail in JP-A 2003-169668 (EP1,298,200).

<2> Enhancing L-Cysteine Biosynthetic Enzyme Activity

L-cysteine-producing ability may be imparted to a bacterium by enhancing an activity of an L-cysteine biosynthetic enzyme. Enhancing an L-cysteine biosynthetic enzyme can be performed by enhancing, for example, an activity of serine acetyltransferase (SAT). Enhancing the SAT activity in cells of an *Escherichia* bacterium can be attained by increasing a copy number of a SAT gene. For example, a recombinant DNA can be prepared by ligating a gene fragment encoding SAT to a vector that functions in *Escherichia* bacteria, preferably a multi-copy type vector, and transforming a host *Escherichia* bacterium with the vector.

The SAT gene of the present invention may be derived from *Escherichia* bacteria or from any other organism. The cysE SAT gene has been cloned from a wild-type *Escherichia coli* strain and an L-cysteine-secretion mutant strain, and the nucleotide sequence has been elucidated (Denk, D. and Boeck, A., J. General Microbiol., 133, 515-525 (1987)).

Therefore, a SAT gene can be obtained by PCR utilizing primers based on the nucleotide sequence (SEQ ID NO: 31) from a chromosomal DNA of *Escherichia* bacterium (see JP11-155571A). Genes encoding SAT derived from other microorganisms can also be obtained in a similar manner. The SAT gene may be able to hybridize to a DNA having the nucleotide sequence of SEQ ID NO: 31 under stringent conditions, and also may encode a protein having SAT activity, which catalyzes the activation of L-serine by acetyl-CoA.

A chromosomal DNA can be prepared from a bacterium, which is a DNA donor, by the method of Saito and Miura (refer to H. Saito and K. Miura, Biochem. Biophys. Acta, 72, 619 (1963); Text for Bioengineering Experiments, Edited by the Society for Bioscience and Bioengineering, Japan, pp. 97-98, Baifukan, 1992).

In order to introduce the PCR-amplified DNA fragment containing a SAT gene into an *Escherichia* bacterium, vectors typically used for protein expression can be used. Examples of such vectors include pUC19, pUC18, pHSG299, pHSG399, pHSG398, RSF1010, pBR322, pACYC184, pMW219, and so forth.

Introduction of a recombinant vector containing the SAT gene into *Escherichia* bacterium can be attained by methods typically used for transformation of *Escherichia* bacteria, for example, the method of D. A. Morrison (Methods in Enzymology, 68, 326 (1979)), a method of treating recipient cells with calcium chloride so as to increase the permeability for DNA (Mandel, M. and Higa, A., J. Mol. Biol., 53, 159 (1970)), and so forth.

Increasing a copy number of the SAT gene can also be achieved by introducing multiple copies the gene into the chromosomal DNA of an *Escherichia* bacterium. To introduce multiple copies of the SAT gene into the chromosomal DNA of an *Escherichia* bacterium, homologous recombination may be carried out by targeting a sequence which exists on a chromosomal DNA in multiple copies. As sequences which exist on a chromosomal DNA in multi-copies, repetitive DNA or an inverted repeat which exists at the ends of a transposable element can be used. Furthermore, as disclosed in J2-109985A, it is also possible to incorporate a SAT gene into a transposon, and allow it to be transferred so that multiple copies of the gene are introduced into the chromosomal DNA.

Besides the aforementioned gene amplification technique, amplification of the SAT activity can also be attained by replacing an expression regulatory sequence such as a promoter of the SAT gene on a chromosomal DNA or on a plasmid with a stronger one (JP1-215280A). For example, lac promoter, trp promoter, trc promoter, and so forth are known as strong promoters. Substitution of an expression regulatory sequence can also be attained by, for example, gene substitution utilizing a temperature-sensitive plasmid.

Furthermore, it is also possible to substitute several nucleotides in the promoter region of the SAT gene, resulting in modification of the promoter to make it stronger as disclosed in WO00/18935. Expression of the SAT gene is enhanced by such substitution or modification of a promoter, and thereby the SAT activity is enhanced. These modifications of expression regulatory sequence may be combined with the increase of a copy number of SAT gene.

Furthermore, when a suppression mechanism exists for SAT gene expression, enhancing the expression can also be enhanced by modifying an expression regulatory sequence or a gene involved in the suppression so to eliminate or reduce the suppression.

The intracellular SAT activity of an *Escherichia* bacterium can also be increased by modifying an *Escherichia* bacterium to harbor SAT which has reduced or eliminated feedback inhibition by L-cysteine (henceforth also referred to as "mutant-type SAT"). Examples of the mutant-type SAT include SAT having a mutation replacing the methionine at a position 256 of wild-type SAT (SEQ ID 32) with an amino acid other than lysine and leucine, or a mutation deleting a C-terminal region of SAT from the methionine at a position 256 and thereafter. Examples of the amino acid other than lysine and leucine include the 17 kinds of amino acid residues which constitute ordinary proteins with the exceptions of methionine, lysine, and leucine. Preferably, isoleucine can be mentioned. A site-specific mutagenesis technique can be used to introduce a desired mutation into a wild-type SAT gene. As a mutant-type SAT gene, a mutant-type cysE encoding a mutant-type SAT of *Escherichia coli* is known (WO97/15673 and JP11-155571A). *Escherichia coli* JM39-8 strain harboring plasmid pCEM256E, which contains a mutant-type cysE encoding a mutant-type SAT in which the methionine at a position 256 is replaced with glutamic acid (*E. coli* JM39-8 (pCEM256E), private number: AJ13391), has been deposited at the National Institute of Bioscience and Human-Technology, Agency of Industrial Science and Technology (currently, National Institute of Advanced Industrial Science and Technology, International Patent Organism Depositary, Central 6, 1-1, Higashi 1-Chome, Tsukuba-shi, Ibaraki-ken, 305-8566, Japan) on Nov. 20, 1997 under the accession number of FERM P-16527. The original deposit was converted to an international deposit in accordance with the Budapest Treaty on Jul. 8, 2002, and given the accession number of FERM BP-8112.

Furthermore, an *Escherichia* bacterium can be modified to contain a mutant-type SAT by introducing a mutation into a chromosomal SAT gene which prevents feedback inhibition by L-cysteine. The mutation can be introduced by ultraviolet irradiation or a mutagenizing agent used for usual mutagenesis treatment such as N-methyl-N'-nitro-N-nitrosoguanidine (NTG) or nitrous acid.

SAT which is resistant to feedback inhibition by L-cysteine used in the present invention may be a SAT protein modified to be resistant to feedback inhibition, and may also be a SAT protein with a native resistance to feedback inhibition. SAT of *Arabidopsis thaliana* is known not to suffer from feedback inhibition by L-cysteine and can be suitably used in the present invention. pEAS-m is known (FEMS Microbiol. Lett., 179 453-459 (1999)) as a plasmid containing SAT gene derived from *Arabidopsis thaliana*.

<3> Production of L-Cysteine

L-Cysteine can be efficiently produced by culturing the *Escherichia* bacterium of the present invention obtained as described above in a suitable medium to cause accumulation of L-cysteine in the culture medium, and collecting the L-cysteine from the culture medium. Although L-cysteine produced by the method of the present invention may contain cystine in addition to reduced-type cysteine, the target substances produced by the method of the present invention include cystine and a mixture of reduced-type cysteine and cystine.

As culture media, ordinary media containing a carbon source, nitrogen source, sulfur source, inorganic ions, and other organic components, if required, can be used. As carbon sources, saccharides such as glucose, fructose, sucrose, molasses, and starch hydrolysate, organic acids such as fumaric acid, citric acid and succinic acid can be used. As nitrogen sources, inorganic ammonium salts such as ammonium sulfate, ammonium chloride and ammonium phosphate, organic nitrogen such as soybean hydrolysate, ammonia gas, aqueous ammonia, and so forth can be used. As sulfur sources, inorganic sulfur compounds, such as sulfates, sulfites, sulfides, hyposulfites, and thiosulfates can be used. As organic trace amount nutrients, it is desirable to add required substances such as vitamin B1, yeast extract, and so forth in appropriate amounts. In addition to these components, potassium phosphate, magnesium sulfate, iron ions, manganese ions, and so forth may be added in small amounts if required.

The culture is preferably performed under aerobic conditions for 30 to 90 hours. The culture temperature is preferably controlled at 25° C. to 37° C., and pH is preferably controlled at 5 to 8 during the culture. To adjust the pH, inorganic or organic, acidic or alkaline substances, ammonia gas, and so forth can be used. Collecting L-cysteine from the culture medium can be attained by, for example, an ordinary ion exchange resin method, precipitation, and other known methods, or combinations thereof.

EXAMPLES

Hereinafter, the present invention will be explained in detail by the following non-limiting examples.

Strains cysE-deficient *Escherichia coli* JM39 (F+cysE51 tfr-8) (Denk, D. and Bock, A., J. Gene. Microbiol., 133, 515-525 (1987)) was used to identify a gene encoding a protein having CD activity.

To evaluate L-cysteine productivity of the CD-gene-disrupted strains, the following strains were used: JM39ΔtnaA, JM39ΔmetC, JM39ΔcysM, JM39ΔmalY, and JM39ΔcysK as a single-CD-gene-disrupted strain; JM39ΔtnaAΔmetC and JM39ΔcysKΔcysM as a double-CD-gene-disrupted strain; JM39ΔtnaAΔmetCΔcysMΔmalY as a quadruple-CD-gene-disrupted strain; and JM39ΔtnaAΔmetCΔcysKΔcysMΔmalY as a quintuple-CD-gene-disrupted strain. In the production of L-cysteine, a total of six strains, including JM39, single-CD-gene-disrupted strains of JM39ΔtnaA, JM39ΔmetC, JM39ΔcysM, and JM39ΔmalY, and quadruple-CD-gene-disrupted strain JM39ΔtnaAΔmetCΔcysMΔmalY, all of which harbors pEAS-m, a plasmid containing SAT gene of *Arabidopsis thaliana* (FEMS Microbiol. Lett., 179 (1999) 453-459) were used.

Plasmids

A plasmid library containing 4,388 kinds of genes (whole ORF fragments) of *E. coli* was used to identify a gene encoding a protein having CD activity (4,388 kinds of plasmids were respectively dispensed into the wells of forty eight 96-well plates). The plasmid library covers all of the 4,388 kinds of ORF fragments of *E. coli* located downstream to the lac promoter in the pCA24N vector and the expression of each ORF is induced by IPTG. For gene disruption, plasmid pEL3 (K. A. Armstrong et al., J. Mol. Biol. (1984) 175, 331-347) was used to construct pEL3gdtnaA, pEL3gdmetC, pEL3gdcysM, pEL3gdcysK, and pEL3gdmalY. The construction of the plasmids will be described below.

Culture Media

For transformation and culture of *E. coli*, LB medium was used as a complete medium, and M9 medium (6 g/L Na$_2$HPO$_4$, 3 g/L KH$_2$PO$_4$, 0.5 g/L NaCl, 0.25 g/L MgSO$_4$.7H$_2$O, 0.015 mg/L CaCl$_2$.4H$_2$O, 4 g/L glucose, and 0.001 g/L thiamine hydrochloride) was used as a minimum medium. Ampicillin (Amp) was added if necessary. In some experiments, LB liquid medium to which 10 to 30 mM cysteine was added was used. Unless otherwise described, the culture was performed at 37° C. For the culture of cysteine production (30 g/L glucose, 10 g/L NH$_4$Cl, 2 g/L KH$_2$PO$_4$, 1 g/L MgSO$_4$.7H$_2$O, 10 mg/L FeSO$_4$.7H$_2$O, 10 mg/L MnCl$_2$.4H$_2$O, and 20 g/L CaCO$_3$) sodium thiosulfate was added to the culture. The same medium was used to determine the quantity of cysteine.

Preparation of Cell Extract

The preparation of the cell extract from the cultured cells was performed by sonication. The composition of the buffer used for the sonication was 100 mM Tris-HCL (pH 8.6), 100 mM DTT ((±)-Dithiothreitol), and 10 mM PLP (pyridoxal phosphate).

Composition of Native-PAGE Gel and Procedure of Native-PAGE (Polyacrylamide Gel Electrophoresis Under Undenatured Conditions)

Since it was necessary to separate proteins in the cell extract under an undenatured state, Native-PAGE gel containing no SDS was prepared for the purpose of identifying and ascertaining a protein having CD activity, confirming the construction of the CD-gene-disrupted strains, and so on, by CD activity staining described hereinbelow. The composition of the Native-PAGE gel for three gel sheets was 6.4 ml of Acrylamide/Bisacrylamide/amide (37:5:1), 6.7 ml of 1 M Tris-HCl (pH 8.7), 6.8 ml of dH$_2$O, 100 µl of 10% APS (Ammonium persulfate), and 10 µl of TEMED (N,N,N,N'-Tetra-methyl-ethylenediamine) for 12.5% gel, and 5.1 ml of Acrylamide/Bisacrylamide/amide (37:5:1), 6.7 ml of 1 M Tris-HCl (pH 8.7), 8.1 ml of dH$_2$O, 100 µl of 10% APS, and 10 µl of TEMED for 10% gel. The concentrated gel was 4.5% and its composition for three gel sheets was (0.7 ml of Acrylamide/Bisacrylamide/amide (37:5:1), 0.75 ml of 1 M Tris-HCl (pH 6.8), 4.52 ml of dH$_2$O, 30 µl of 10% APS, and 5 µl of TEMED. The Native-PAGE was performed using a mini-slab electrophoretic apparatus (AEV-6500, manufactured by ATTO), and a mixture of 30 µg to 50 µg of cell extract and 2-fold Native-PAGE buffer was applied to the gel. The electrophoresis was performed at 200 V and 20 mA/gel for 2 hours to 4 hours. The composition of 1 liter of the electrophoresis buffer was 14.43 g of L-glycine and 3.0 g of Tris, and the buffer was adjusted to pH 8.6.

CD Activity Staining

A CD activity staining method was used for specifically visualizing and detecting the existence of a protein having CD activity. As described in section 1-5, after proteins in the cell extract had been separated by electrophoresis, the gel was immersed in the CD activity staining solution and left to stand at room temperature from several hours to overnight with shaking to detect the protein band having CD activity. The composition of 100 ml of the CD activity staining solution was 1.21 g of Tris, 0.372 g of EDTA, 0.605 g of L-cysteine, 50 mg of BiCl$_3$ (bismuth chloride), and 200 µl of 10 ml PLP, and the solution was adjusted to pH 8.6. The CD activity staining was performed based on the principle that cysteine contained in the CD activity staining solution is degraded into pyruvic acid, ammonia, and H$_2$S at the site where a protein having CD activity separated with Native-PAGE exists on the gel. The generated H$_2$S reacts with bismuth chloride (BiCl$_3$) contained in the CD activity staining solution to form bismuth sulfide (Bi$_2$S$_3$), which exhibits a black color band.

Identification of a Gene Encoding a Protein Having CD Activity Using a Plasmid Library Containing *E. coli* Whole Genes The forty-eight 96-well plates on which respective plasmids were dispensed were grouped into 5 plates such as 1 to 5, 6 to 10 . . . , and nine kinds of mixed plasmid solutions obtained from five plates (each containing 480 kinds of plasmids) were prepared. The mixed plasmid solutions were used to transform JM39 strains and about 10,000 colonies of transformants were stocked in glycerol. The nine kinds of glycerol-stock solutions were inoculated into LB medium containing chloramphenicol (Cm) and 0.01 mM IPTG and cultured. Then, cell extract was prepared and subjected to Native-PAGE. CD activity staining was performed to detect which mixed plasmid solution contained a candidate gene encoding a protein having CD activity. The population containing a candidate gene presumed to encode a protein having CD activity was downsized to a population of 480 kinds of plasmids, and then, further downsizing of the population to that of 96 kinds of plasmids was performed. 480 kinds of the plasmids were divided into five groups of 96 to prepare five kinds of mixed plasmid solutions. JM39 strains were transformed with the mixed plasmid solutions and about 6,000 colonies of the transformants were stocked in glycerol. Thereafter, the transformants were cultured and CD activity staining was performed to confirm if the mixed plasmid solution contains a candidate gene encoding a protein having CD activity. After the population containing a candidate gene presumed to encode a protein having CD activity was downsized to 96 kinds of plasmids, the population was further reduced to 8 kinds of plasmids. Finally, eight proteins were each expressed from the 8 kinds of plasmids and CD activity staining was performed to confirm if they are the target protein having CD activity.

Construction of Plasmids for CD Gene Disruption

To disrupt each CD gene, five kinds of plasmids for gene disruption, i.e., pEL3gdtnaA, pEL3gdmetC, pEL3gdcysM, pEL3gdcysK, and pEL3dgmalY were constructed using plasmid pEL3 having a temperature-sensitive replication origin. The preparation methods for these plasmids are described below. That is, using the genome of *E. coli* JM39 as a template, two kinds of 300 to 700 bp DNA fragments each covering a part of the respective CD gene was amplified by PCR. The DNA fragments were designated homologous region DNA fragments-A and -B, respectively. The primers used are described in FIG. 2. For the amplification of the homologous region DNA fragment-A, CD gene disruption primers-1 and -2 were used, and for the amplification of the homologous region DNA fragment-B, CD gene disruption primers-3 and -4 were used. These primers had a restriction enzyme recognition site at the 5'-side so that the amplified homologous region DNA fragments contain restriction enzyme recognition sites at both ends. After treatment with appropriate restriction enzymes of both fragments A and B (KpnI, HindIII, or EcoRI), both the enzyme-treated fragments were ligated to each other to form a template for preparing CD gene disruption fragments. The CD gene disruption fragments were prepared in large amounts by PCR using the CD gene disruption primers-1 and -4. The disruption fragments and pEL3 were treated with the restriction enzyme BamHI and ligated to each other to construct the CD gene disruption plasmids. The construction was confirmed by DNA sequencing.

Disruption of CD Gene

A CD gene-disrupted strain was constructed from *E. coli* JM39 strain with the disruption plasmid as described in section 1-9. First, disruption plasmids were introduced into JM39 to obtain transformants. The limiting temperature for temperature-sensitive plasmid pEL3 is 42° C. Alternatively, the non-limiting temperature, a temperature not higher than the limiting temperature, for the plasmid is generally 37° C., which is an ordinary culture temperature for *E. coli*. However, the culture was performed at 30° C. in this experiment to ensure the temperature sensitivity of the plasmid. Then, after each transformant was cultured overnight at 30° C. in an LB+Amp medium, the culture broth was diluted to $10^3$-fold, and 200 µl of the diluted solution was spread on the LB+Amp plate. Culture was performed at 42° C., which is the temperature at which the plasmid becomes unreplicable and the growth of the transformants is inhibited by Amp, and therefore no colonies form. Thereby, homologous recombination occurred between each disrupted fragment on the plasmid with suppressed replication and a homologous region on the chromosome of the JM39 strain. This allowed the whole length of the disruption plasmid to be incorporated into the chromosome. Then, the recombinant strain was selected which was able to form an Amp resistant colony by incorporation of the disruption plasmid. The incorporation of the disruption plasmid into the chromosome was confirmed by PCR using FW and RV of each CD gene disruption primer as described in FIG. 2. The colony having a confirmed disruption plasmid incorporated into the chromosome was cultured in an LB liquid medium to cause further homologous recombination. This was done so that the disrupted fragment remains on the chromosome and the fragment containing a plasmid sequence and a chromosomal gene is removed. The transformants were subcultured several times in an LB liquid medium. Then, the culture broth was spread on an LB agar medium after dilution to a concentration that would cause 200 to 300 colonies to form on the LB agar medium. The colonies were replicated on an LB plate and an LB+Amp agar plate to select for Amp-sensitive colonies. By performing colony PCR using FW and RV primers, CD-gene-disrupted strains having only the disrupted fragment on the chromosome were selected.

The CD-gene-disrupted strains were subjected to CD activity staining and disappearance of the CD activity due to gene disruption was confirmed. A multiple CD-gene-disrupted strain was constructed by repeating the operation of disrupting the target CD genes.

Measurement of Total CD Activity (Sulfide/$H_2S$ Quantification)

The total CD activity in the cell extract was measured by determining the amount of hydrogen sulfide ($H_2S$) generated by degradation of cysteine by CD. A strain was cultured in 5 ml of LB medium and 5 ml of LB+10 mM cysteine medium at 37° C. overnight, and then the cell extract was prepared as in the section 2-2-4. The composition of the buffer used for measuring the CD activity was 100 mM Tris-HCl (pH 8.6), 100 µM DTT, 10 mM PLP, 2 µM L-cysteine. 10 ml of the cell extract was added to 1 ml of the buffer and the reaction was carried out at 30° C. for 10 minutes. A standard curve was prepared by adding 10 µl aliquots of water, or 10 µl of 0.1 mM, 0.2 mM, or 2 mM of $Na_2S$ to the buffer and the mixture was incubated in the same way. After completion of the reaction, 100 ml of 20 mM N,N-dimethyl-p-phenyldiamine sulfate (in 7.2 N HCl) and the same amount of 30 mM $FeCl_3$ (in 1.2 N HCl) were added, vigorously mixed, and left to stand in the dark for 15 minutes. Iron chloride acts as an oxidizing agent under acidic conditions adjusted by hydrochloric acid, and the N,N-dimethyl-p-phenyldiamine sulfate reacts with a sulfide in the sample to form a thiazine dye. As a result, Methylene Blue exhibits a greenish blue or blue color. The mixture was left to stand for 15 minutes, then, OD650 of the reaction mixture was measured and the activity was calculated by defining an amount of enzyme giving 1 µmol $H_2S$ as 1 U.

Cysteine Production Culture

Each of the obtained transformants was inoculated in a Sakaguchi flask containing 20 ml of C1 medium with sodium thiosulfate (15 g/L thiosulfuric acid), and cultured at 37° C. The amount of L-cysteine in the supernatant after 24, 48, 72, and 96 hours was quantified. The amount of L-cysteine was measured as a total amount of reduced cysteine and cystine by the bioassay using *Leuconostoc mesenteroides* (Tsunoda, T. et al., Amino acids, 3, 7-13 (1961)).

2. Results 2-1. Confirmation of Existence of a Protein Having CD activity in *E. coli*

To confirm the existence of a protein having CD activity in *E. coli*, a cell extract of JM39 strain was prepared and subjected to Native-PAGE, and electrophoresis was performed for about 2 hours to separate proteins, which was then subjected to activity staining. FIG. 1 shows the results. Five bands exhibiting CD activity were detected. This experiment indicates that at least five kinds of proteins having CD activity are present in *E. coli*. Of those, two were identified as tryptophanase (TNase) and cystathionine-β-lyase (CBL) by amino acid sequencing analysis (JP 2003-169668A). To identify the remaining three, the following experiments were performed.

2-3. Identification of the Unidentified CD Proteins Using *E. coli* Total Gene Plasmid Library The genome of *E. coli* is presumed to have a total of 4,388 genes (ORF). Using the *E. coli* whole ORF library in which all ORFs were inserted into each plasmid, the operation for identification of a protein having a CD activity was repeated by the procedure described in the section 1-7. By detecting the band of the unidentified CD protein by CD activity staining, the population of plasmids containing a gene encoding an unidentified CD protein was reduced from 4,388 kinds to 480 kinds, 96 kinds, and 8 kinds, sequentially. Finally, the selected 8 kinds of plasmids were analyzed and the proteins encoded by the cysM gene, cysK gene, and malY gene were found to be the unidentified CD proteins. The cysM gene of *E. coli* has been reported to encode O-acetyl L-serine sulphydrylase-B (OASS-B) (see J. Bacteriol. 172 (6), 3351-3357 (19890)). The cysK has been reported to encode O-acetyl L-serine sulphydrylase (OASS-A) (Mol. Microbiol. 2 (6), 777-783 (1988)). Furthermore, it has been reported that the malY gene encodes a MalY protein which is a regulatory factor for maltose metabolism pathway gene group and has a conformation close to that of CBL and catalyzes the C—S lyase reaction (EMBO J. 2000, March; 19(5):831-842).

2-4. Confirmation of CD Activity

The OASS-B, OASS-A, and MalY identified in section 2-3 were confirmed to have the CD activity by overexpressing the genes in the JM39 strain. That is, when the respective genes were overexpressed and protein bands of cell extract were analyzed by CD activity staining, the stained band was denser than the band of the control JM strain, indicating that each gene encodes a protein having CD activity.

2-5. Construction of CD-Gene-Disrupted Strain

Then, each CD-gene-disrupted strain was constructed. Methods of preparing JM39ΔtnaA and JM39ΔmetC strains are disclosed in JP 2003-169668A. First, disruption plasmids pEL3gdtnaA, pEL3gdmetC, pEL3gdcysM, pEL3gdcysK, and pEL3gdmalY for disrupting tnaA, metC, cysM, cysK, and malY, respectively, were constructed and introduced into the JM39 strain to construct single-disrupted strains by homologous recombination. Furthermore, the gene disruption step was repeated to prepare multiple-disrupted strains, such as a quadruple disrupted strain JM39ΔtnaAΔmetCΔcysMΔmalY in which tnaA, metC, cysM, and malY were disrupted. After the operation of gene disruption, gene disruption was confirmed based on the length of the DNA fragment amplified by colony PCR. Furthermore, it was confirmed by CD activity staining that the CD activity of a protein encoded by each gene was eliminated due to gene disruption.

2-6. Measurement of Total CD Activity

According to the method in the section 1-11, the total CD activities of all the CD-gene-disrupted strains used in this experiment were measured. The results are shown in Table 1. As a result, comparison of the total CD activity of each strain cultured in LB medium with that of the parent strain JM39 indicated a decrease in the CD activity for all the disrupted strains. Comparison of the activity of the multiple-disrupted strain with the activity of JM39 indicated a considerable decrease in the CD activity except for JM39ΔcysKΔcysM. The decrease in the CD activity in multi-disrupted strains was significant as compared with the decrease in the activity in each single-disrupted strain. The activity of JM39ΔcysKΔcysM decreased as compared with the activities of single-disrupted strains. Then, the total CD activity of the CD-gene-disrupted strain cultured in a medium to which cysteine was added was analyzed. In the strains other than JM39ΔtnaA, the CD activity of the strain cultured in a cysteine-containing medium increased considerably as compared with the CD activity of the same strain cultured in an LB medium.

TABLE 1

| Strain | medium total CD activity (mU/mg) | |
|---|---|---|
| | LB | LB + 10 mM L-cysteine |
| JM39 | 20.6 ± 0 | 27.6 ± 0 |
| JM39ΔtnaA | 15.7 ± 0 | 14.1 ± 0 |
| JM39ΔmetC | 15.0 ± 0 | 27.6 ± 0.46 |
| JM39ΔcysK | 18.2 ± 0.52 | 29.9 ± 0 |
| JM39ΔcysM | 17.9 ± 0.46 | 27.8 ± 0 |
| JM39ΔmalY | 15.3 ± 0 | 27.1 ± 0.46 |
| JM39ΔtnaAΔmetC | 9.6 ± 0 | 16.2 ± 0 |
| JM39ΔcysKΔcysM | 17.2 ± 0.58 | 27.0 ± 0 |
| JM39ΔtnaAΔmetCΔcysMΔmalY | 9.1 ± 0.46 | 19.6 ± 0 |
| JM39ΔtnaAΔmetCΔcysKΔcysMΔmalY | 8.7 ± 0.46 | 11.5 ± 0 |

Figure 3:
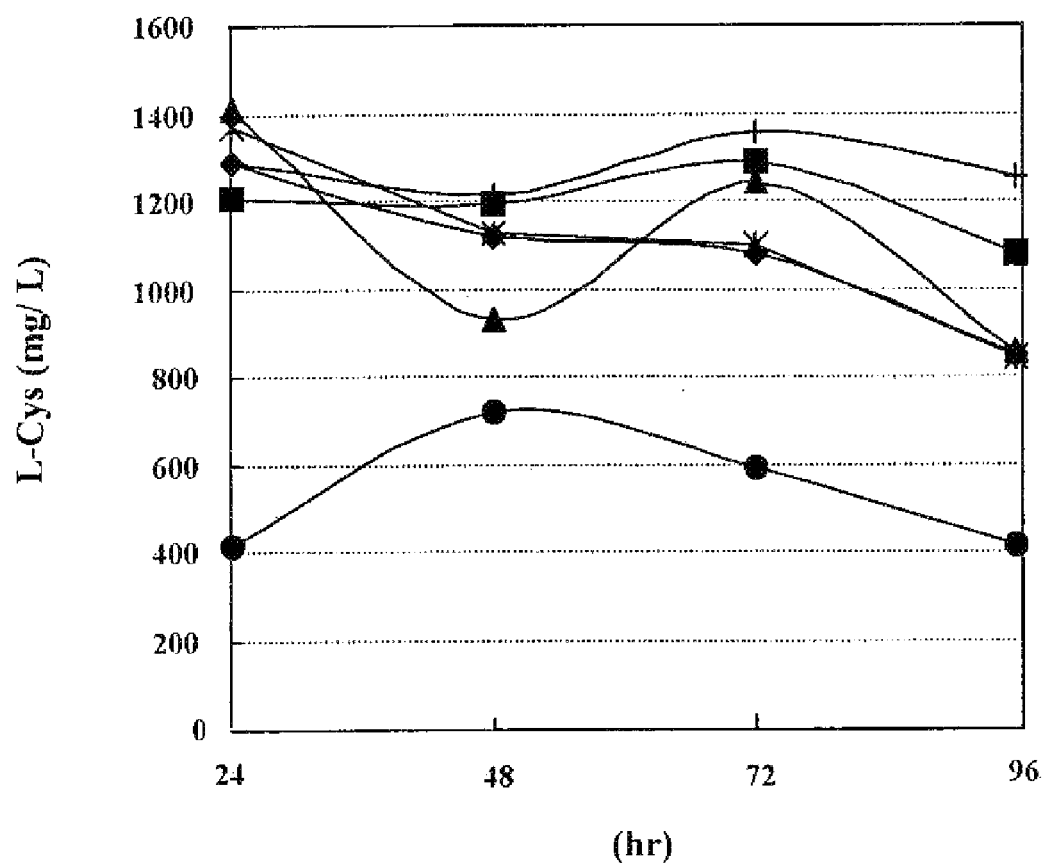
FIG. 3 shows L-cysteine-producing ability of the control strain and each CD gene-disrupted strain; JM39 (●), JM39ΔtnaA (■), JM39ΔmetC (▲), JM39Δcysm (*), JM39ΔmalY (+), and JM39ΔtnaAΔmetCΔmalYΔcysM (♦).

2-7. Cysteine Production Using CD-Gene-Disrupted Strains pEAS-m, a plasmid containing SAT-m gene of *A. thaliana*, was introduced into a total of six strains, i.e., a control JM39 strain, four single-CD-gene-disrupted strains of JM39ΔtnaA, JM39ΔmetC, JM39ΔcysM, and JM39ΔmalY, and a quadruple-CD-gene-disrupted strain of JM39ΔtnaAΔmetCΔmalYΔcysM, and the transformants were used for the production of cysteine. Cysteine production culture was performed according to the method in the section 1-12 and the amount of produced cysteine was quantified. Time courses of the amounts of produced cysteine of the control strain and each of the CD-gene-disrupted strain per growth (growth: value of $OD_{562}$) are shown in Table 2 and FIG. 3. The growth decreased slightly in the case of JM39ΔtnaA but the growth of other disrupted strains was substantially the same as that of the control strain JM39.

TABLE 2

| Strain | L-Cys (mg/L) hr | | | |
|---|---|---|---|---|
| | 24 | 48 | 72 | 96 |
| JM39 | 416 ± 96 | 720 ± 161 | 587 ± 164 | 415 ± 111 |
| JM39ΔtnaA | 1206 ± 26 | 1195 ± 95 | 1287 ± 74 | 1077 ± 124 |
| JM39ΔmetC | 1408 ± 98 | 930 ± 47 | 1243 ± 101 | 853 ± 13 |
| JM39ΔmalY | 1291 ± 95 | 1213 ± 93 | 1359 ± 87 | 1256 ± 75 |
| JM39ΔcysM | 1369 ± 67 | 1123 ± 148 | 1100 ± 66 | 840 ± 56 |
| JM39ΔtnaAΔmetCΔmalYΔcysM | 1291 ± 21 | 1117 ± 21 | 1080 ± 13 | 847 ± 69 |

The L-cysteine production of the respective gene-disrupted strains exceeded the value of the control strain JM39. Therefore, the disruption of the CD genes to inhibit the CD activity is effective for increasing the production of cysteine. When cysK gene-disrupted strains were used, almost no cysteine could be obtained when a cysteine production C1 medium containing sodium thiosulfate was used.

INDUSTRIAL APPLICABILITY

By using the bacteria of the present invention, L-cysteine can be produced efficiently. L-cysteine and its derivatives are useful in the fields of medicine, cosmetics, foods, and the like.

While the invention has been described in detail with reference to preferred embodiments thereof, it will be apparent to one skilled in the art that various changes can be made, and equivalents employed, without departing from the scope of the invention. Each of the aforementioned documents, including the foreign priority documents, Japanese Patent No. 2004-060483 filed on Mar. 4, 2004, is incorporated by reference herein in its entirety.

The invention claimed is:

1. A method of producing L-cysteine comprising:
   A) culturing an *Escherichia* bacterium in a medium, and
   B) collecting L-cysteine from the medium or the bacterium, wherein said bacterium contains a gene encoding O-acetylserine sulphydrylase B, and wherein said gene is modified so that cysteine desulfhydrase activity is reduced or eliminated as compared to the cysteine desulfhydrase activity in a bacterium containing a non-modified gene.

2. The method according to claim 1, wherein said gene encoding O-acetylserine sulphydrylase B is disrupted.

3. The method according to claim 1, wherein activity of an L-cysteine biosynthetic enzyme is enhanced.

4. The method according to claim 3, wherein said L-cysteine biosynthetic enzyme is serine acetyltransferase.

5. The method according to claim 4, wherein said serine acetyltransferase is resistant to feedback inhibition by L-cysteine.

6. The method according to claim 1, wherein said *Escherichia* bacterium is *Escherichia coli*.

* * * * *

UNITED STATES PATENT AND TRADEMARK OFFICE
CERTIFICATE OF CORRECTION

| | | |
|---|---|---|
| PATENT NO. | : 8,114,649 B2 | Page 1 of 1 |
| APPLICATION NO. | : 12/635404 | |
| DATED | : February 14, 2012 | |
| INVENTOR(S) | : Takagi et al. | |

It is certified that error appears in the above-identified patent and that said Letters Patent is hereby corrected as shown below:

Section (62) on the front page of the U.S. Patent should be amended as follows:

Division of application No. 11/070,084, filed on Mar. 3, 2005, now abandoned.

Signed and Sealed this
Nineteenth Day of June, 2012

David J. Kappos
*Director of the United States Patent and Trademark Office*